United States Patent [19]
Braeuning et al.

[11] Patent Number: 6,033,076
[45] Date of Patent: *Mar. 7, 2000

[54] VISUAL FIELD TESTING VIA TELEMEDICINE

[75] Inventors: Johannes Braeuning, Ostfildern; Stefan Schueller, Petershagen, both of Germany; Dariusz Wroblewski; Richard J. McClure, both of San Diego, Calif.; R. Kemp Massengill, Leucadia, Calif.

[73] Assignees: Virtual-Eye.com, Inc., Leucadia; Orincon Corp., San Diego, both of Calif.

[*] Notice: This patent is subject to a terminal disclaimer.

[21] Appl. No.: 09/203,729

[22] Filed: Dec. 2, 1998

Related U.S. Application Data

[63] Continuation-in-part of application No. 09/179,112, Oct. 26, 1998, which is a continuation-in-part of application No. 08/864,331, May 28, 1997, Pat. No. 5,898,474, which is a continuation of application No. 08/700,754, Jul. 31, 1996, Pat. No. 5,864,384

[60] Provisional application No. 60/067,521, Dec. 4, 1997, provisional application No. 60/089,817, Jun. 19, 1998, and provisional application No. 60/090,214, Jun. 22, 1998.

[51] Int. Cl.$^7$ ........................................................ A61B 3/02
[52] U.S. Cl. ............................................. 351/224; 351/246
[58] Field of Search ................................... 351/222, 224, 351/226, 246

[56] References Cited

U.S. PATENT DOCUMENTS

| | | | |
|---|---|---|---|
| 5,061,059 | 10/1991 | Horn | 351/223 |
| 5,325,136 | 6/1994 | Salibello et al. | 351/243 |
| 5,565,949 | 10/1996 | Kasha, Jr. | 351/224 |
| 5,758,651 | 6/1998 | Nygard et al. | 128/741 |
| 5,867,494 | 2/1999 | Krishnaswamy et al. | 370/352 |

FOREIGN PATENT DOCUMENTS

| | | |
|---|---|---|
| 0 850 661 | 7/1998 | European Pat. Off. . |
| 0 856 333 | 8/1998 | European Pat. Off. . |
| 0 857 455 | 8/1998 | European Pat. Off. . |

OTHER PUBLICATIONS

Arnold, D. B., The Oculomotor Integrator: Testing of a Neural Network Model; Dec. 1995; Exp Brain Res (1997) 113; pp. 57–74.

Brigatti, Luca; Automatic Detection of Glaucomatous Visual Field Progression with Neural Networks; Jun. 1997; Arch Ophthalmol, vol. 115; pp. 725–728.

Brigatti, L.; Neural Networks to Identify Glaucoma with Structural and Functional Measurements; Nov. 1995; American Journal of Ophthalmology (1996) 121; pp. 511–521.

Gardner, G.; Automatic Detection of Diabetic Retinopathy Using an Artificial Neural Network; A Screening Tool; Jun. 1996; British Journal of Ophthalmology (1996) 80; pp. 940–944.

Goldbaum, Michael H.; Interpretation of Automated Perimetry for Glaucoma by Neural Network; Mar. 1994; Investigative Ophthalmology & Visual Science, Aug. 1994, vol. 35, No. 9; pp. 3362–3373.

Levin, Leonard A.; Neural Network Differentation of Optic Neuritis and Anterior Ischaemic Optic Neuropathy; May 1996; British Journal of Ophthalmology (1996)80; pp. 835–839.

(List continued on next page.)

*Primary Examiner*—Huy Mai
*Attorney, Agent, or Firm*—Gerald W. Spinks

[57] ABSTRACT

A method and an apparatus for the performance and auto-interpretation via the Internet, or other telemetric vehicle, of the visual function test parameters obtained during interactive visual field screening utilizing a local display screen. Such interactive testing and instantaneous autointerpretation of visual field performance utilizing a local display screen, via telemedicine, are utilized to screen for glaucoma and other neurological disorders affecting the visual system. Telemedicine, such as via the Internet, allows the system to be employed on a world-wide basis, including areas where physicians are not present.

14 Claims, 2 Drawing Sheets

OTHER PUBLICATIONS

Spenceley, S. E.; Visual Field Analysis Using Artificial Neural Networks; Feb. 1994; Ophthal. Physiol. Opt., 1994, vol. 14; pp. 239–248.

Uchida, Hideya; Detection of Structural Damage from Glaucoma with Confocal Laser Image Analysis; Jul. 1996; Investigative Ophthalmology & Visual Science, Nov. 1996, vol. 37, No. 12; pp. 2393–2401.

Alboliras, E.; Transmission of Full–Length Echocardiographic Images over ISDN for Diagnosing Cogenital Heart Disease; 1996; Telemedicine Journal vol. 2, No. 4; pp. 251–258.

Angood, P.; Internet–based Telemedicine: A Practical Tool?; 1998; Medicine Meets Virtual Reality; pp. 383–384.

Bashshur, R.; *Telemedicine;* date unknown; pp. 309–347.

Bekker, M.; *Exploring Telemedicine;* date unknown; 6 pages.

Bethke, W.; The Internet vs. Glaucoma; Nov. 1997; Review of Ophthalmology; p. 19.

Blackwell, N.; Telemedicine Ophthalmology Consultation in Remote Queensland; Apr. 1997; Medical Journal of Australia; 6 pages.

Defense Department Awards Telemedicine Ophthalmolmic Technology Contract; May 1997; Telemedicine and Virtual Reality; p. 53.

Dicon brochure; *The Future: Visual Fields Across the Information Superhighway;* Aug. 1998; 1 page.

Grigsby, J.; Effects and Effectiveness of Telemedicine; 1995; Health Care Financing Review; pp. 1–18.

Grigsby, J.; Telemedicine: Where It Is anda Where It's Going; Jul. 1998; Annals of Internal Medicine; pp. 123–127.

Heneghan, C.; Teleophthalmology at the New York Eye and Ear Infirmary; Dec. 1996; Telemedicine Today; 3 pages.

Heneghan, C.; Ophthalmology Rides Wave of Telemedicine; May 1997; Ophthalmology Times; 2 pages.

Heneghan, C.; Clinical Interaction the Key to Telemedicine; Jun. 1997; Ophthalmology Times; 5 pages.

Lindberg, D.; Medicine and Health on the Internet; Oct. 21, 1998; Journal of the American Medical Association, vol. 280, No. 15; pp. 1303–1304.

Marcus, D.; Telemedicine Diagnosis of Eye Disorders by Direct Ophthalmoscopy; May 1998; Ophthalmology; pp. 1907–1914.

Mitka, M.; Developing Countries Find Telemedicine Forges Links to More Care and Research; Oct. 21, 1998; Journal of the American Medical Association, vol. 280, No. 15; pp. 1295–1296.

Mutlukan, E.; Visual Field Interpretation with a Personal Computer Based Neural Network; 1994; Eye, vol. 8; pp. 321–323.

Nitzkin, J.; Reliability of Telemedicine Examination; 1997; Telemedicine Journal; pp. 141–157.

Pedersen, S.; Teleconsultation of Patients with Otorhinolaryngologic Conditions; Feb. 1994; Archives of Otolaryngologic Head Neck Surgery, vol. 120; pp. 133, 135, 136.

Sanders, J.; Challenges to the Implementation of Telemedicine; 1995; Telemedicine Journal; pp. 115–123.

Sarasohn–Kahn, J.; Tele–Health; 1996; Medical and Healthcare Marketplace Guide; pp. 43–44.

Schiffman, J.; Practice Makes Perfect: Devising Technical Specs for Tele–ophthalmology; Jun. 1997; Telemedicine; 5 pages.

Singer, H.; New Perimetry Algorithm Uses Artificial Intelligence to Shorten Test Time; Nov. 1996; publication unknown; 2 pages.

Telemedicine Targets Mammographic Services; Dec. 1997; Biophotonics International; 1 page.

Teleophthalmology Clinic Gets a Workout; Nov. 1997; Telemedicine and Virtual Reality; p. 132.

Casson, E.; Temporal Modulation Perimetry: The Effects of Aging and Eccentricity on Sensitivity in Normals; Jul. 1992; Investigative Ophthalmology & Visual Science, vol. 34, No. 11; pp. 3096–3102.

Lachenmayr, B.; Light–Sense, Flicker and Resolution Perimetry in Glaucoma: A Comparative Study; May 1990; Graefe's Archive of Clinical and Experimental Ophthalmology; pp. 246–251.

Lachenmayr, B.; Diffuse and Localized Glaucomatous Field Loss in Light–Sense, Flicker and Resolution Perimetry; Aug. 1990; Graefe's Archive of Clinical and Experimental Ophthalmology; pp. 267–273.

Smith, D.; Using Frequency Doubling Technology; Oct. 1998; Ophthalmology Management; pp. 76–78, 82.

VISUAL FIELD TESTING VIA TELEMEDICINE

CROSS REFERENCE TO RELATED APPLICATIONS

This is a continuation-in-part patent application of U.S. patent application Ser. No. 09/179,112, filed on Oct. 26, 1998, and entitled "Automated Visual Function Testing Via Telemedicine" which is a continuation-in-part of prior application Ser. No. 08/864,331, filed on May 28, 1997, U.S. Pat. No. 5,898,474, which is a continuation of prior application Ser. No. 08/700,754, filed on Jul. 31, 1996, U.S. Pat. No. 5,864,384. This application also claims the benefit of earlier filed U.S. Provisional Application Ser. No. 60/067,521, filed on Dec. 4, 1997, and entitled "Automated Visual Function Testing in Virtual Reality"; U.S. Provisional Application Ser. No. 60/089,817, filed on Jun. 19, 1998, and entitled "Telemedicine for Autointerpretation of Visual Field Testing"; and U.S. Provisional Application Ser. No. 60/090,214, filed on Jun. 22, 1998, and entitled "Telemedicine for In-Home Visual Field Screening".

STATEMENT REGARDING FEDERALLY SPONSORED RESEARCH OR DEVELOPMENT

"Not Applicable"

BACKGROUND OF THE INVENTION

1. Field of the Invention

This invention is in the field of visual field screening.

2. Background Information

On a world-wide basis, glaucoma is one of the leading causes of blindness. Unlike cataract blindness, which is correctable with modem surgical techniques, blindness from glaucoma is permanent. The target organ of glaucoma is the optic nerve, which transmits signals of light from the retina to the brain. No known method is available for repairing, or transplanting, an injured optic nerve. Millions upon millions of patients throughout the world have glaucoma and are completely unaware of this. The particularly sad aspect of glaucoma blindness is that it is generally preventable with proper diagnosis and treatment.

A major diagnostic problem is that, in many areas of the world, medical resources are scarce to the point of being virtually nonexistent. Therefore, many diseases which are readily treatable, sadly, go about their devastating business completely unchecked. Glaucoma, which causes absolute, total blindness when untreated, is no exception.

A second major diagnostic problem is that visual loss from glaucoma is, almost without exception, painless. The patient is unaware of the ravages of glaucoma until it is too late. With the use of an instrument called a "tonometer" to measure the intraocular pressure, the diagnosis can be made whenever the pressure within the eye is significantly elevated. However, tonometry is not available in many parts of the world; and many patients have the "low-tension" form of glaucoma in which the intraocular pressure is completely normal. Therefore, reliance upon tonometry, in areas of the world where this is available, frequently leads to a blatantly false sense of security. The patient is told that glaucoma is not present, when, in reality, the disease is insidiously attacking the patient's optic nerve, causing irreversible neurological damage to the visual system.

Because of the limitations associated with tonometry, most eye physicians attest that visual field testing is mandatory for glaucoma diagnosis and treatment. In fact, visual field testing is currently considered to be the gold standard for measuring the function of the optic nerve and the presence, or absence, of glaucoma. Visual field testing is generally an expensive proposition, however, with significant fees being charged for each test. Often, there is a physician or optometric examination charge in addition to the fee for the visual field test itself. Another major hurdle is that the patient must make an appointment for an eye examination, which is sometimes difficult. Additionally, since glaucoma is generally painless and totally devoid of symptoms until late stages of the disease, for the vast majority of people, no concrete motivation is present to seek professional help when nothing hurts. The upshot of this is that the diagnosis of glaucoma is all too frequently never made until it is too late.

Furthermore, in countries which are economically disadvantaged, visual field testing machines are prohibitively expensive.

BRIEF SUMMARY OF THE INVENTION

Utilizing the patient's home computer, or some other video display system, and telemedicine, such as the Internet and other telemetric modalities, the present invention provides an extremely inexpensive vehicle for addressing the serious problem of glaucoma blindness throughout the world.

Screening software programs can be accessed by the patient's personal computer (or by any computer available to the patient, such as that of a friend or of a local clinic) from the Internet or other telemetric vehicle. Alternatively, a computer monitor, a television screen, or some other local video display system may be used, with the software programs being operated entirely on a remote computer to generate the desired stimuli on the local video display system. Therefore, the entire testing process can be performed via long-distance transmission vehicles, such as, but not limited to, the Internet, or an optical fiber network, thus providing, telemetrically, not only essentially instantaneous autointerpretation, but also telemetric monitoring of the patient's performance of the test in real time.

At least gross telemetric monitoring is available by monitoring the speed of the patient's responses, as well as the response itself and whether it makes rational sense, based upon nomograms of typical patient visual behavior. Computers or systems available to the patient with audio capability, such as an audio card, can provide audio feedback stimuli, such as voice, or a tone or series of tones, to monitor the test performance in real-time and provide interactive feedback to the patient. A patient can receive a "grade" correlated with demonstrated responsiveness and concentration ability, thus indicating whether the patient's performance is satisfactory for meaningful autointerpretation.

A central world-wide monitoring and data collection station, or a series of stations in different geographic areas, can link the system and provide multiweb-like integration. As international long-distance communication becomes more and more accessible and affordable, it is preferable that one station have global capability. The Internet provides virtually instantaneous, extremely affordable, world-wide access. The present telemedicine system is "intelligent," in that ongoing data accumulation and analyses thereof improve the computational model and provide, over time, increasingly more accurate identification of more subtle disease processes.

The novel features of this invention, as well as the invention itself, will be best understood from the attached drawings, taken along with the following description, in which similar reference characters refer to similar parts, and in which:

DETAILED DESCRIPTION OF THE INVENTION

Relying solely upon the patient's access to a computer or other video display system, the present invention provides a quick and easy world-wide visual field screening system via the Internet, or via some other long-distance telemedicine vehicle. All that is required is for the patient to access the software programs which in real-time interactively present, monitor, and instantaneously autointerpret the visual field screening test. The software programs can be accessed via telemedicine, such as "going on-line" on the Internet.

Early attempts at providing computer assisted visual field displays included work at NASA's Ames Research Laboratory during the late 1980's, where a computer graphic environment was created for the display of binocular field of view and retinal visual projections. These mapping efforts were, however, in no way associated with the use of interactive telemedicine.

In the preferred embodiment, the proposed invention utilizes "frequency doubling" and "noise-field campimetry" software programs for quick and efficient visual screening of the patient on his or her own display system. These two types of programs are well known in the art.

An alternative embodiment of the proposed invention includes flicker and temporal modulation perimetry, as described in work published by Lachenmayr, and work published by Casson. High temporal flicker frequencies stimulate, on a preferential basis, ganglion cells projecting to the magnocellular layers of the lateral geniculate body. These axons are called M-cell fibers, and it is these nerve fibers which are postulated to be preferentially damaged in glaucoma. Detection of damage to M-cell fibers, then, helps make the diagnosis of glaucoma in its earlier stages. Flicker perimetry is an excellent tool with patients who also have cataract formation. The Lachenmayr method uses the highest frequency of flicker, called the "critical flicker frequency", which is detected for a 100 percent contrast flicker target. The Casson method employs a group of frequencies, such as temporal frequencies of 2, 8, and 16 Hz.

Another alternative embodiment of the proposed invention employs color-on-color visual field strategies. This embodiment requires that the patient have access to a color video monitor or color television. One such strategy, currently known in the art, is called "short wavelength automated perimetry". The advantage of this strategy is that defects are believed to become apparent several years before being noted on standard automated perimetry visual field tests.

Still another alternative embodiment of the proposed invention employs motion, or "kinetic" perimetry strategies, which are currently well known in the art.

Figure 1:
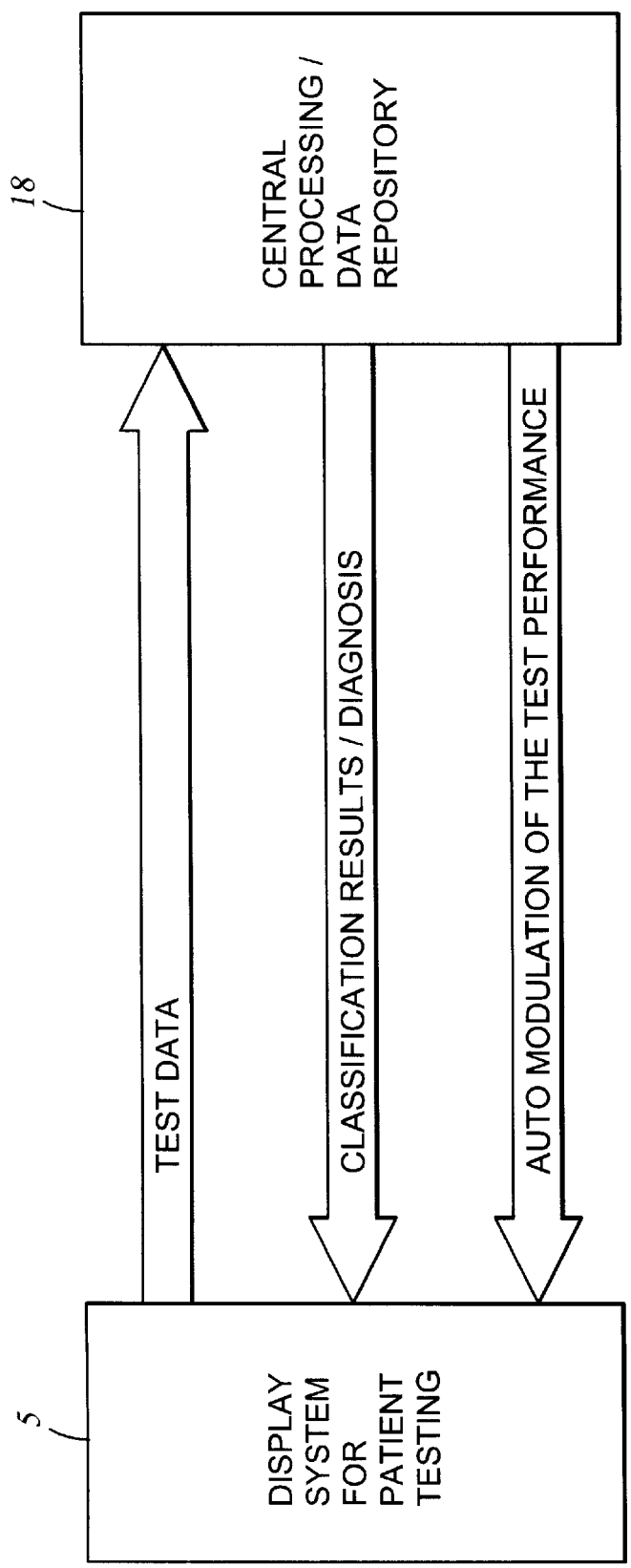
FIG. 1 is a schematic diagram of the information flow in the system of the present invention.

The system of the present invention, as illustrated in FIG. 1, includes a local visual field test apparatus 5, which can include a display screen, such as a television or a computer monitor. The local apparatus may also include a local computer. It is recognized that using the patient's display system may not provide quite the degree of accuracy of the best available perimeter systems. Extremely subtle visual field changes are more difficult to notate on a computer or television display. Deficiencies include the fact that ambient lighting conditions will vary from one person's home to another. The "texture" and luminosity of one person's display screen will vary from that of another person. Some display screens have adjustable "brightness," and some do not. "Gamma calibration", a procedure well known in the art, is one strategy which can be used in the software incorporated in the present invention, as a standardization aid.

Visual field testing utilizing a video display as the visual fixation source may not equal the accuracy attainable with a full threshold first-class globe perimeter; nevertheless, the present invention can achieve an initial accuracy level of 75 to 80 percent, and maybe more. Providing this degree of test accuracy via a world-wide telemetric system, such as the Internet, for interactive real-time performance and for instantaneous autointerpretation of visual screening test results, will play a major role in eliminating world-wide glaucoma blindness. By providing a preliminary diagnosis virtually instantaneously and telemetrically, the patient can be educated to seek help from the medical profession. A screening "preliminary" diagnosis can be then be confirmed, and, if glaucoma is present, proper glaucoma treatment can be instituted. The proposed invention may well spare millions and millions of patients throughout the world blindness and the ravages of undiagnosed glaucoma.

In addition to testing for glaucomatous damage to the optic nerve, visual field testing with the present invention can also be used to test for a variety of neurological disorders, including cerebrovascular accidents ("strokes"), trauma, brain tumors, and other diseases. Generally speaking, strokes and major neurological brain diseases cause quite large visual field deficits, and the proposed invention will readily help make the diagnosis of these disorders.

With the huge data base developed by a large-scale, world-wide telemedicine system, leading international experts on glaucoma and other neurological diseases can be employed to improve the accuracy of the entire system.

Investigational work has been done on the use of neural nets "trained to interpret the visual fields from an automated perimeter," as described in "Interpretation of Automated Perimetry for Glaucoma by Neural Net," by Goldbaum, et al. Spenceley, et al., have also published work in the field in an article entitled, "Visual Field Analysis Using Artificial Neural Networks." Brigatti, Hoffman, and Caprioli have worked with neural networks for glaucoma identification, as described in their article entitled, "Neural Networks to Identify Glaucoma With Structural and Functional Measurement." These works are limited to conventional globe-like perimeter systems.

Some of the inventors of the present invention have also developed a method and an apparatus for automatic, computerized interpretation of the visual function test parameters obtained in a head-mounted display virtual realty testing system. The data produced by the testing system are automatically reviewed and correlated with previously-determined patterns recognized to be "normal" or "abnormal," and clinical diagnoses for pathological conditions are thereby suggested to the clinician. Telemedicine can be utilized to receive test data from the patient and to transmit the test interpretation, including the suspected diagnosis, or diagnoses, and recommendations for further clinical correlation or for further ancillary tests. Telemedicine can be employed to monitor interactively and automatically, in real time, the patient's performance of the visual field test.

The system of the present invention similarly uses clustering algorithms, linear and non-linear mapping algorithms, and pattern recognition algorithms, either individually or as a combination thereof. The remote computing system consists of a central processing system and data repository 18, as shown in FIG. 1. A database of empirical, semi-empirical, or simulated visual field test data is used to build a model of the visual field test data. This model, when applied to previously unseen test results, is capable of automatically interpreting and classifying the test data in terms of the presence and/or severity of abnormal (diseased) regions and states.

The data processing portion of the system provides not only the classification of the visual field test data in terms of presence or absence of all disease, or any particular disease (e.g., glaucoma), but also may assign a probability of detection and/or a numerical value indicating the severity of the disease. This provides a tool for monitoring disease progression.

The automatic interpretation portion of the system may be a binary classification system, which will indicate the presence or absence of a particular disease, such as glaucoma, or a multi-class system, which provides recognition and classification of a large variety of possible visual field disorders, including, but not limited to, neurological tumors, cerebrovascular accidents and strokes, optic nerve disorders, compression syndromes of the optic nerve or optic chiasm, demyelinating diseases, and diseases of the retina.

The system of the present invention utilizes the results of visual stimuli consisting of dots, symbols, shapes, or patterns, etc., with or without color, depending upon the capability of the patient's display screen. These are presented to the patient in the form, preferentially, of such visual screening programs as frequency doubling and noise-field campimetry, but also including standard automated perimetry visual testing schemes such as those used by the Humphrey Field Analyzer. Noise-field campimetry can be used to present visual stimuli to the patient utilizing the entire display screen, called "full-field" noise-field campimetry. Also, a completely new technique called "focal" or "segmental" noise-field campimetry can also be employed as a visual testing strategy in the proposed invention. In this technique, only a focal area of the display screen is utilized to test visual function responses of the patient. These focal areas of noise-field stimuli can be moved from location to location upon the display screen, or from quadrant to quadrant. Incorporating focal noise-field campimetry as a testing strategy for the proposed invention provides an extremely efficient method to determine significant visual field loss.

Regardless of the particular testing strategy utilized, these visual stimuli, as described in the preceding paragraph, are converted into numerical representation for data processing. Other inputs, resulting from standard pre-processing of the test data, such as visual field indices, can also be employed by the interpretation system. Inclusion of all available individual components of perimetric examination is useful for proper clinical interpretation of the visual test examination.

Thus, the information provided to the automated interpretation system may include:

ancillary data, such as pupil size during testing (as estimated or measured by an independent observer of the patient), the patient's age, and visual acuity (which can be measured for near vision by the testing program);

reliability indices, such as fixation behavior and accuracy, and response fluctuation;

visual field indices, such as average deviation of sensitivity at each test location from age-adjusted normal population values, the index of the degree of irregularity of visual field sensitivity about the normal slope, and sensitivity analysis of clusters of points;

results of point-by-point comparison of test results with age-matched normal population values;

results of high-pass resolution perimetry (with resolution limitations ascribed, among other considerations, to the innate quality and performance capabilities of the patient's computer system and display monitor);

results of flicker and temporal modulation perimetry;

results of color-on-color perimetry testing strategies, using a color video monitor or television;

results of motion, or "kinetic", perimetry visual field testing strategies; and, results of pattern discrimination perimetry, including frequency doubling, noise-field campimetry (both "full field" noise-field campimetry, as well as "focal" noise-field campimetry), and other currently available, or to-be-developed, tests.

The implementation may be in the form of a single-level system or a hierarchical system. In the single-level system, all the input data which are deemed relevant for the interpretation task, are inputted and processed simultaneously. In the hierarchical system, different input data types are modeled by dedicated separate sub-systems, and these outputs are subsequently fused through a suitable computational architecture, such as a neural network, to produce the final classification result.

Figure 2:
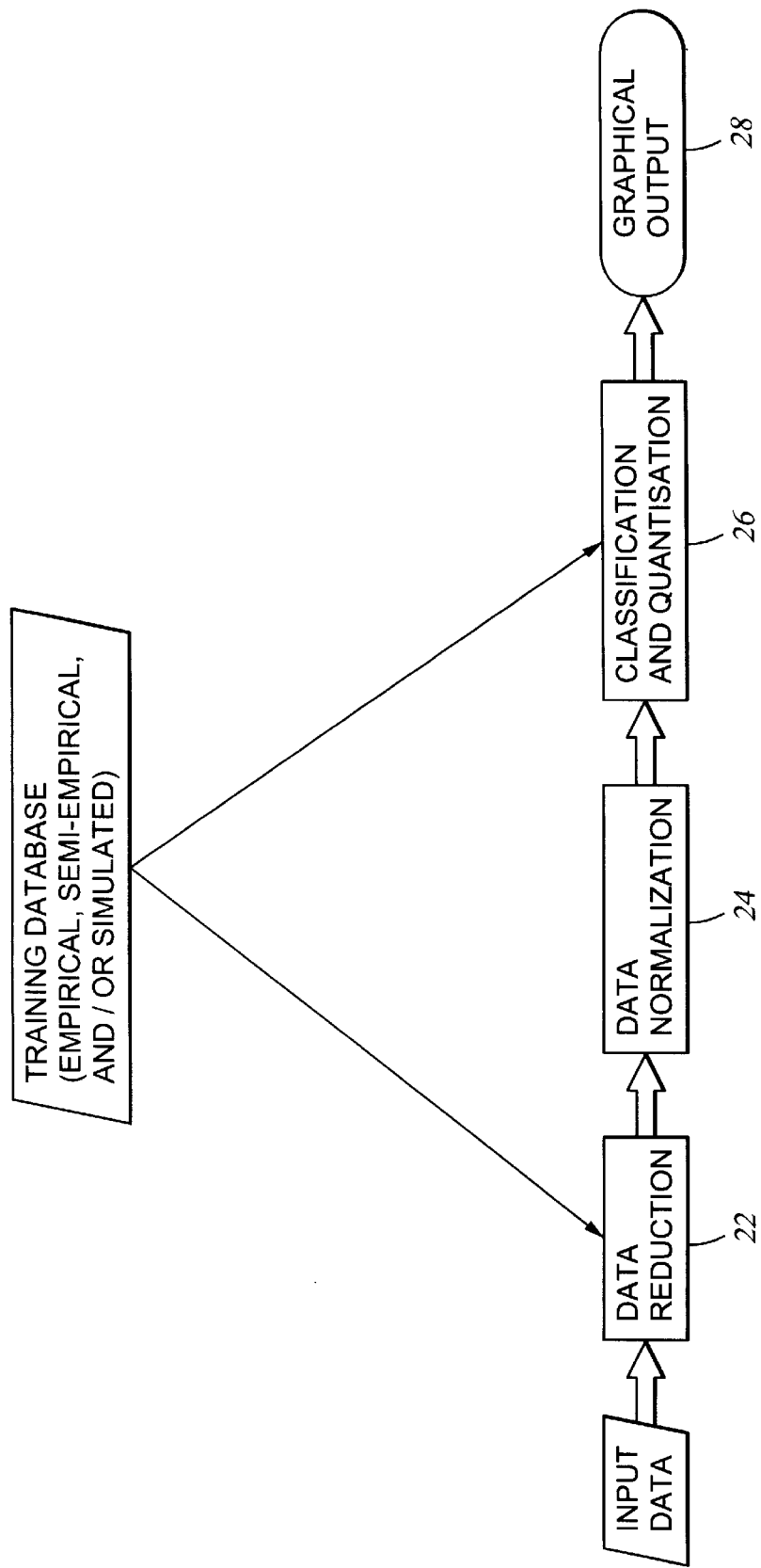
FIG. 2 is a schematic diagram of the automatic interpretation portion of the system of the present invention.

The automatic interpretation system, shown in FIG. 2, can consist of the following modules:

clustering/data reduction module 22, which may employ singular value decomposition, principal component analysis, learning vector quantization, or other clustering or data size reduction methods;

data normalization module 24;

data classification module 26, which performs pattern recognition, classification, and quantification of the visual field test data through non-linear or linear mapping. This function may be accomplished through the use of multilayer perceptron neural network and other neural network architectures, or through non-linear, multivariate, or linear regression of the data, or by multivariate statistical classifiers or discriminators (such as Bayesian classifiers);

output module 28, creating a graphical representation of the visual field test data, such as isopter/scotoma plots, or gray scale or color-coded plots, with superimposed identification of the regions that the system classified as abnormal.

The automatic interpretation system is an expert system automatically trained on a set of empirical, semi-empirical, and/or simulated data. The construction of a proper training database is essential for achieving good performance of the interpretation system, including good sensitivity and specificity. The training database may contain all, or any, of the following types of visual field data:

empirical data, i.e., data obtained for patients with normal and abnormal visual fields;

semi-empirical data, i.e., data obtained by modification of the empirical data, as described above, by:

emphasizing or de-emphasizing certain aspects of the visual field test to bring out the characteristic features of certain diseased states;

adding noise or measurement uncertainty component(s) which may be associated with a real visual field examination;

any other modification of the visual field test data and their associated classification; and, simulated data, i.e., data that are constructed to simulate the real-world results of a visual field test for both normal and abnormal visual fields.

The data produced by the testing system are automatically reviewed and correlated with previously-determined patterns recognized to be "normal" or "abnormal," and clinical diagnoses for pathological conditions are thereby suggested. Telemedicine is utilized to receive test data from the patient and to transmit the test interpretation, including the suspected diagnosis, or diagnoses, and recommendations for further clinical correlation or for further ancillary tests. Telemedicine is also employed to monitor interactively and automatically, in real time, the patient's performance of the visual field test.

The content of the software is dictated by the need to provide technically acceptable protocols, such as for examining the field of view and deficiencies thereof, utilizing measurements of thresholds for pattern discrimination, sensitivity to light intensity, or, if desired and available on the patient's display monitor, color. The preferred embodiment includes frequency doubling and noise-field campimetry (both "full field" campimetry, and "focal" noise-field campimetry), as these are very amenable to testing on a display monitor screen. Active feedback sensing can alert the system to patient loss of attention, for notation and reiteration of test stimuli. Individual test points are reiterated when a result is found to be inconsistent with a predetermined norm. Audio feedback stimuli can present a voice, or a tone or series of tones, to monitor the test performance in real-time and to provide interactive feedback. Each eye is tested individually by occluding the non-tested eye.

Specific instructions are given to the patient to establish the proper geometric conditions for test performance, such as the recommended distance from the eyes to the patient's display screen, and head placement relationhip thereto. It is important that the dimensions of the patient's display screen be known. These dimensions, as well as the display screen's manufacturer and model number, can be readily transmitted to the central station computer, so that the software can provide necessary viewing distance instructions and other pertinent recommendatons. Widening the field of view is easily accomplished by simply decreasing the distance from the patient's eyes to the display monitor.

While the particular invention as herein shown and disclosed in detail is fully capable of obtaining the objects and providing the advantages hereinbefore stated, it is to be understood that this disclosure is merely illustrative of the presently preferred embodiments of the invention and that no limitations are intended other than as described in the appended claims.

We claim:

1. A visual field testing system comprising:

a video display screen for viewing by a patient at a local site;

a computing means located at a site remote from said local site, said remote computing means being programmed to generate visual stimuli for presentation on said local display screen, to monitor a patient's responses to said visual stimuli, to provide real-time feedback to said responses, and to provide diagnostic information to a patient;

an automatically-trained expert system at said remote site connected to said remote computing means for receiving data on said responses from a patient, for instantaneously interpreting said responses, and for providing interpretation of said responses to said remote computing means; and a data transmission system between said local and remote sites for transmitting data between said local display screen and said remote computing means.

2. A visual field testing system as recited in claim 1, wherein said local video display screen comprises a television screen.

3. A visual field testing system as recited in claim 1, further comprising a computing means at said local site, wherein:

said local video display screen comprises a video monitor connected to said local computing means;

said remote computing means displays said visual stimuli on said video monitor via said local computing means;

said patient responses are transmitted to said remote computing means via said local computing means; and said feedback and said diagnostic information are transmitted to a patient via said local computing means.

4. A visual field testing system as recited in claim 1, wherein said remote automatically-trained expert system comprises a neural network.

5. A visual field testing system as recited in claim 1, wherein said data transmission system between local and remote sites comprises the internet.

6. A visual field testing system comprising:

a plurality of local computers including video monitors for viewing by patients at a plurality of testing sites;

a response means at each testing site for activation by a patient at said testing site;

a computer at a site remote from said testing sites, said remote computer being programmed to generate visual stimuli via said local computers for presentation on said video monitors, to monitor patients' responses to said visual stimuli, to provide real-time feedback to said responses, and to provide diagnostic information to patients;

a neural network at said remote site connected to said remote computer for receiving data on said responses from a patient, for instantaneously interpreting said responses, and for providing interpretation of said responses to said remote computer; and a data transmission system between said local testing sites and said remote site for transmitting data between said local computers and said remote computer.

7. A visual field testing system as recited in claim 6, wherein said local response means comprises a switch for activating an electrical signal.

8. A method for performing visual field testing, said method comprising:

providing a display screen for viewing by a patient at a local site, a response means for activation by a patient at said local site, a computer at a site remote from said local site, an autointerpretation system at said remote site, and a data transmission system between local and remote sites;

generating visual stimuli for presentation on said local display screen;

monitoring a patient's responses to said visual stimuli;

providing real-time feedback to said responses;

providing data on said responses to said remote autointerpretation system;

instantaneously interpreting said responses with said remote autointerpretation system;

providing interpretation of said responses to said remote computer; and providing diagnostic information to a patient with said remote computer, via said data transmission system.

9. A method for performing visual field testing, as recited in claim 8, wherein:

said visual stimuli are generated by said remote computer for presentation on said local display screen, via said data transmission system;

said patient's responses to said visual stimuli are monitored with said remote computer, via said data transmission system; and said real-time feedback to said responses is provided by said remote computer, via said data transmission system.

10. A method for performing visual field testing, as recited in claim 8, wherein:

said local display screen comprises a local computer with a video monitor;

said visual stimuli are generated by said remote computer for presentation on said local video monitor, via said local computer and said data transmission system;

said patient's responses to said visual stimuli are monitored with said remote computer, via said local computer and said data transmission system; and said real-time feedback to said responses is provided by said remote computer, via said local computer and said data transmission system.

11. A method for performing visual field testing, as recited in claim 8, wherein:

said local display screen comprises a local computer with a video monitor;

said method further comprises downloading of software from said remote computer to said local computer;

said visual stimuli are generated by said local computer for presentation on said local video monitor;

said patient's responses to said visual stimuli are monitored with said local computer; and said real-time feedback to said responses is provided by said local computer.

12. A method for performing visual field testing, as recited in claim 8, wherein said generation of visual stimuli and said automatic interpretation of said responses implement flicker and temporal modulation perimetry strategies.

13. A method for performing visual field testing, as recited in claim 8, wherein said generation of visual stimuli and said automatic interpretation of said responses implement color-on-color visual field strategies.

14. A method for performing visual field testing, as recited in claim 8, wherein said generation of visual stimuli and said automatic interpretation of said responses implement kinetic perimetry strategies.

* * * * *